United States Patent
Hashimoto

(10) Patent No.: US 9,901,336 B2
(45) Date of Patent: Feb. 27, 2018

(54) SUTURE DEVICE

(71) Applicant: OLYMPUS Corporation, Tokyo (JP)

(72) Inventor: Tatsutoshi Hashimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 404 days.

(21) Appl. No.: 14/627,289

(22) Filed: Feb. 20, 2015

(65) Prior Publication Data
US 2015/0230790 A1 Aug. 20, 2015

Related U.S. Application Data

(63) Continuation of application No. PCT/JP2013/071408, filed on Aug. 7, 2013.

(60) Provisional application No. 61/693,028, filed on Aug. 24, 2012.

(51) Int. Cl.
A61B 17/04 (2006.01)
A61B 17/06 (2006.01)

(52) U.S. Cl.
CPC .......... A61B 17/0469 (2013.01); A61B 17/06 (2013.01)

(58) Field of Classification Search
CPC . A61B 17/0469; A61B 17/06; A61B 17/0491; A61B 17/04; A61B 17/0483; A61B 17/0487; A61B 17/0498; A61B 17/0482; A61B 17/0485; A61B 17/0493; A61B 2017/06052; A61B 2017/0488; A61B 2017/049; A61B 2017/0472;
(Continued)

(56) References Cited

U.S. PATENT DOCUMENTS

| 5,814,054 A * | 9/1998 | Kortenbach ....... A61B 17/0469 606/139 |
| 2009/0259233 A1* | 10/2009 | Bogart ............. A61B 17/06004 606/144 |
| 2009/0312773 A1 | 12/2009 | Cabrera et al. |

(Continued)

FOREIGN PATENT DOCUMENTS

| EP | 0 647 431 A2 | 4/1995 |
| JP | H07-155332 A | 6/1995 |

(Continued)

OTHER PUBLICATIONS

Oct. 29, 2013 International Search Report issued in International Application No. PCT/JP2013/071408.
(Continued)

Primary Examiner — Diane Yabut
Assistant Examiner — Erich Herbermann
(74) Attorney, Agent, or Firm — Oliff PLC

(57) ABSTRACT

A suture device is provided with a longitudinal member; a pair of grasping members; a suture needle; a power transmitting member; an opening-closing operating portion; a pair of needle locking portions having a first needle locking member and a second needle locking member and locking or releasing the suture needle to or from the pair of grasping members; a pair of wire members connected to the pair of needle locking portions; a needle locking and operating portion that operates the pair of wire members; a link member having a first end and a second end connected to the pair of wire members; and rotatable support portions that rotatably support the link member.

20 Claims, 11 Drawing Sheets

(58) Field of Classification Search
CPC .... A61B 2017/0474; A61B 2017/0475; A61B 2017/0477
USPC ........................................ 606/145, 144, 139
See application file for complete search history.

(56) References Cited

U.S. PATENT DOCUMENTS

| | | | |
|---|---|---|---|
| 2011/0040308 A1* | 2/2011 | Cabrera | A61B 17/0469 606/144 |
| 2012/0150197 A1* | 6/2012 | Malkowski | A61B 17/0625 606/144 |
| 2012/0215234 A1 | 8/2012 | Chowaniec et al. | |

FOREIGN PATENT DOCUMENTS

| | | |
|---|---|---|
| JP | 2001-500765 A | 1/2001 |
| JP | 2010-005386 A | 1/2010 |
| JP | 2010-505519 A | 2/2010 |
| WO | 98/11829 A1 | 3/1998 |
| WO | 2008/045333 A2 | 4/2008 |

OTHER PUBLICATIONS

Apr. 15, 2016 Extended Search Report issued in European Patent Application No. 13831750.8.

* cited by examiner

SUTURE DEVICE

This application is a Continuation of PCT International Application No. PCT/JP2013/071408, filed on Aug. 7, 2013, whose priority is claimed on provisional U.S. Patent Application No. 61/693,028, filed on Aug. 24, 2012, the contents of both the PCT International Application and the provisional U.S. patent application are incorporated herein by reference.

TECHNICAL FIELD

The present invention relates to a suture device for medical use.

BACKGROUND ART

Conventionally, suture devices for performing suturing within a body are known. For example, an automatic needle pass suture device is disclosed in Published Japanese Translation No. 2001-500765 of the PCT International Publication. The suture device disclosed in Published Japanese Translation No. 2001-500765 of the PCT International Publication has two end effectors and a needle engaged with the end effectors. In this suture device, living body tissue can be sutured through the needle by passing the needle from one end effector of the two end effectors to the other end effector.

SUMMARY OF INVENTION

A suture device related to a first aspect of the present invention includes a longitudinal member which is provided to extend along a longitudinal axis; a cover member which is provided in a distal end of the longitudinal axis and includes an inner space; a pair of grasping members which are held to be capable of opening and closing at a distal end of the inner space; a pair of needle locking portions which are capable of locking a suture needle to the pair of grasping members; a first wire member which has a distal end that is connected to one of the pair of needle locking portions and a proximal end that extend to a proximal end of the longitudinal member and that is continuously provided in the distal end, which is arranged so as to be capable of moving along the longitudinal member, and which has flexibility; a second wire member which has a distal end that is connected to the other of the pair of needle locking portions and a proximal end that extend to a proximal end of the longitudinal member and that is continuously provided in the distal end, which is arranged so as to be capable of moving along the longitudinal members, and which has flexibility; an operating portion which is provided in the proximal end of the first wire member and the second wire member, and which is capable of operating a displacement of the first wire member and the second wire member along the longitudinal member; an annular link member which has a first connecting portion that is connected between the distal end of the first wire member and the operating portion, a second connecting portion that is connected between the distal end of the second wire member and the operating portion, and a body that is connected to the first connecting portion and the second connecting portion, which is held to be capable of rotating at a proximal end of the cover member, and which is provided at an outer periphery of the proximal end of the cover member.

In the suture device related to a second aspect of the present invention based on the above first aspect, the suture device further may include a power transmitting member which is provided to be capable of moving at the inner space of the cover member along the longitudinal member with respect to both of the first wire member and the second wire member and performs the opening and closing operation of the pair of grasping members.

In the suture device related to a third aspect of the present invention based on the above second aspect, the power transmitting member may be provided to be capable of moving inside the link member. The suture device further may include a grasping opening-closing link that is connected to a distal end portion of the power transmitting member and an opening-closing shaft that allows a proximal end of the pair of grasping members to be connected to the grasping opening-closing link and the cover member and that supports so as to be capable of opening and closing of the pair of grasping members.

In the suture device related to a fourth aspect of the present invention based on the above first aspect, when the second wire member is pulled to the operating portion side as the link member is rotated, the first wire member may push one of the pair of needle locking portions to a distal end of the needle locking portion and the second wire member may pull the other of the pair of needle locking portions to the operating portion side, and the suture needle may be passed from one of the pair of grasping member to the other of the pair of grasping members.

In the suture device related to a fifth aspect of the present invention based on the above second aspect, the link member may have a rotatable supporting portion that extends toward the cover member. A central axis of the link member may extend in a direction intersecting the longitudinal axis.

In the suture device related to a sixth aspect of the present invention based on the above first aspect, the longitudinal member may have flexibility. The body may have an annular shape that has a space into which the cover member is insertable.

In the suture device related to a seventh aspect of the present invention based on the above fifth aspect, the first connecting portion and the second connecting portion may be connected to the body, so as to be rotatable with respect to the body, with an axis parallel to the central axis of the rotatable supporting portion as a center of rotation. A hole through which the first wire member is capable of being inserted may be formed in the first connecting portion and a hole through which the second wire member is capable of being inserted may be formed in the second connecting portion.

In the suture device related to an eighth aspect of the present invention based on the above seventh aspect, tubular members, which abut against opening ends of the holes and position the first wire member and the second wire member with respect to the first connecting portion and the second connecting portion, may be attached to the first wire member and the second wire member.

In the suture device related to a ninth aspect of the present invention based on the above first aspect, the longitudinal member may have flexibility. The suture device further may include an opening-closing shaft that supports so as to be capable of opening and closing of the pair of grasping members. A range from a distal end of the first wire member to the opening-closing shaft and a range from a distal end of the second wire member to the opening-closing shaft may be respectively inserted through pipes that are harder than the first wire member and the second wire member.

In the suture device related to a tenth aspect of the present invention based on the above first aspect, the pair of grasping members may have a conical depression for supporting the suture needle. The suture needle may have a conical end that fits into the depression, and a groove portion that is adjacent to the end and has a diameter smaller than the end. The pair of needle locking portions nay have a through-hole through which the end is capable of being inserted, and a locking hole portion that is formed so as to be connected to the through-hole, and has a width that is smaller than the internal diameter of the through-hole and greater than the external diameter of the groove portion.

DESCRIPTION OF EMBODIMENTS

A suture device of an embodiment of the present invention will be described.

Figure 1:
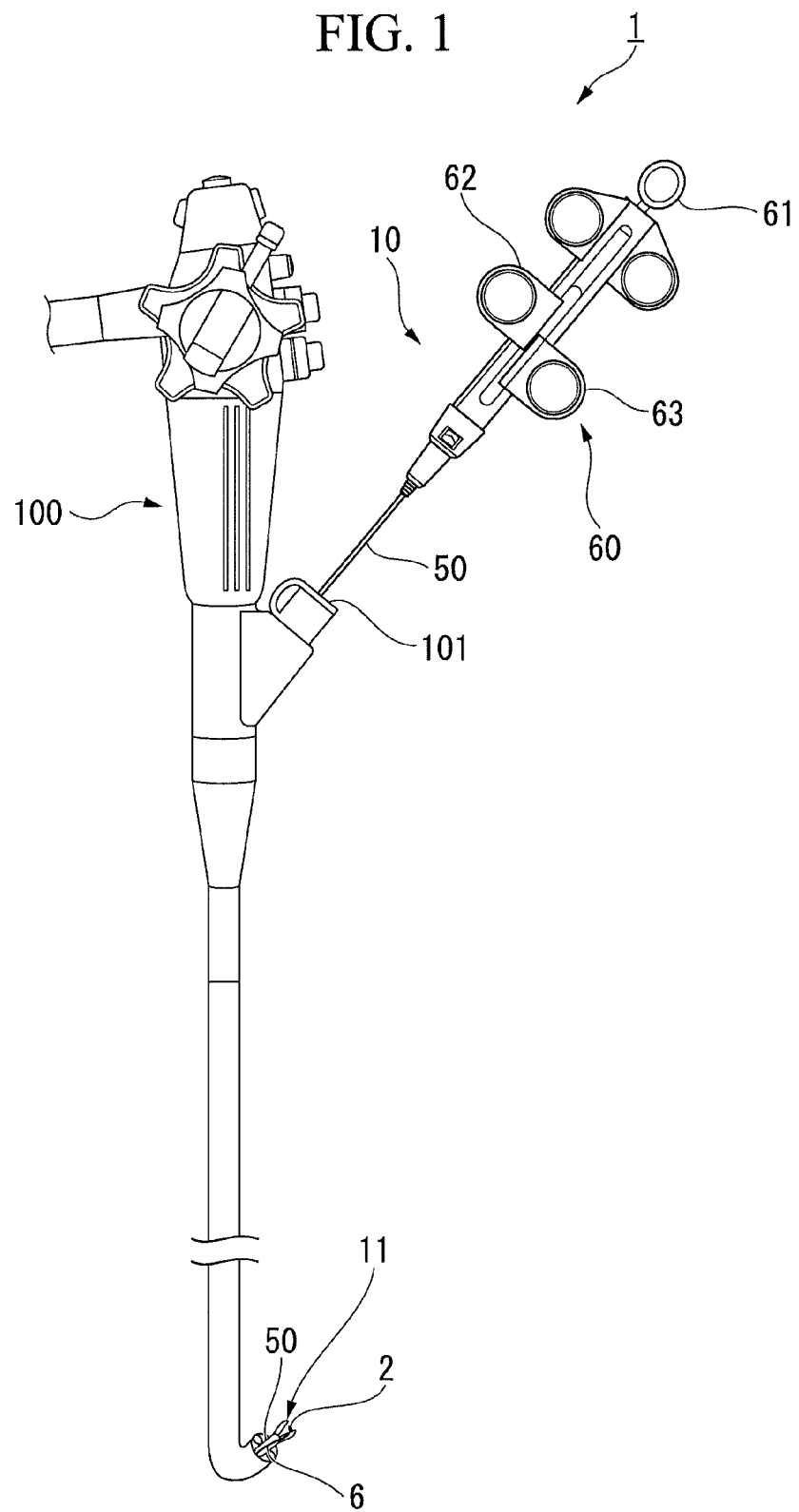
FIG. 1 is an overall view showing a suture device of an embodiment of the present invention.

FIG. 1 is an overall view showing a suture device of an embodiment of the present invention. As illustrated in FIG. 1, the suture device 1 is a device that is used together with an endoscope 100 and sutures living body tissue using a suture 6. The suture device 1 includes a suture needle 2 to which the suture 6 is attached, and an applicator 10 for puncturing living body tissue with the suture needle 2.

Figure 2:
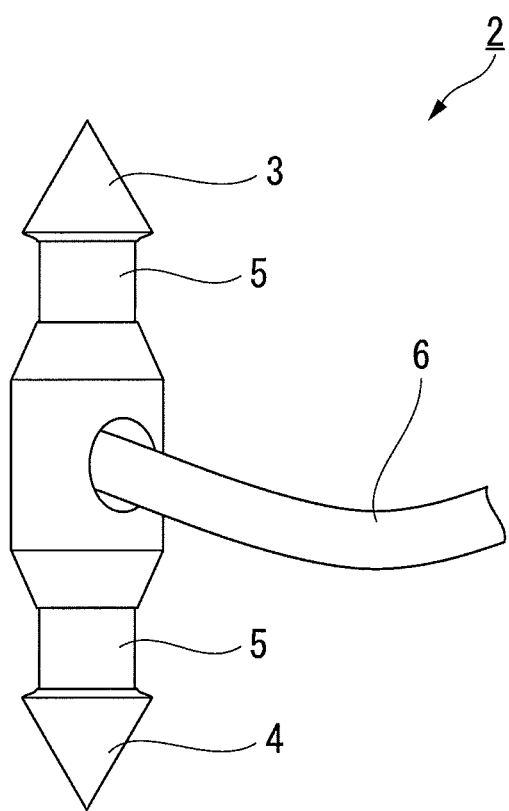
FIG. 2 is a schematic view showing a suture needle.

FIG. 2 is a schematic view showing the suture needle. As illustrated in FIG. 2, the suture needle 2 is a needle having one end (first end) formed in the shape of a cone and the other end (second end) formed sharply. In the present embodiment, the ends 3 (first end) and 4 (second end) of the suture needle 2 are sharply formed in the shape of a cone. That is, both of the ends 3 and 4 of the suture needle 2 can puncture living body tissue. Additionally, two groove portions 5 engaged with a pair of needle locking portions 30 to be described below are formed between the ends 3 and 4 of the suture needle 2. Each groove portion 5 has an external diameter smaller than the maximum external diameter of the conical portion at the end of the suture needle 2. Additionally, an end of the suture 6 is fixed between the respective groove portions 5 at an intermediate portion of the suture needle 2.

As illustrated in FIG. 1, the applicator 10 includes a treatment portion 11, a longitudinal member 50 that has the treatment portion 11 disposed at one end (first end) thereof, and an operating portion 60 disposed at the other end (second end) of the longitudinal member 50. Hereinafter, a description will be made with a side on where the treatment portion 11 is disposed being defined as a distal end side, and a side where the operating portion 60 is disposed being defined a proximal end side, in the applicator 10.

Figure 3A:
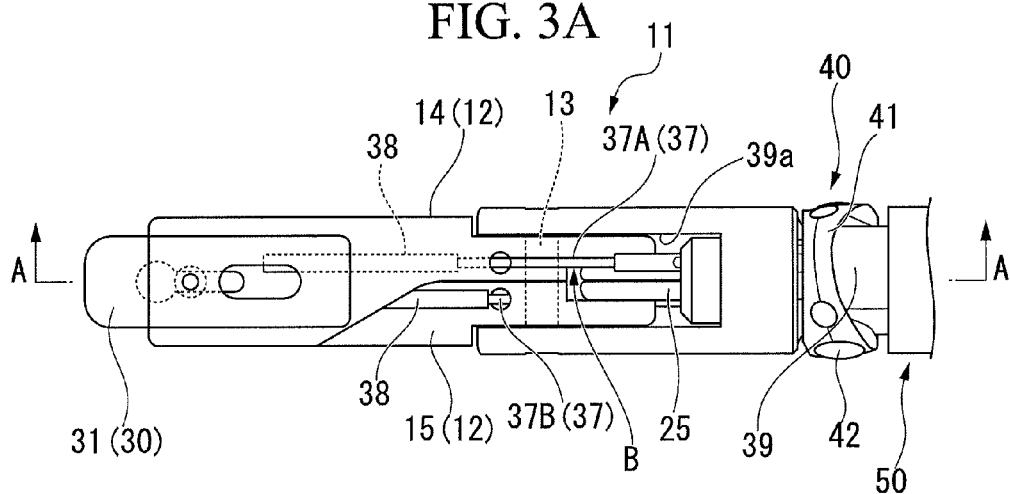
FIG. 3A is a plan view showing a treatment portion in the suture device.
Figure 3B:
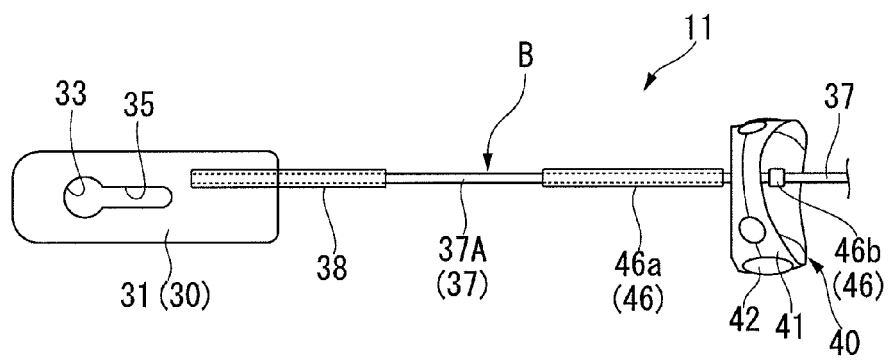
FIG. 3B is a plan view showing the configuration of a portion of the treatment portion.
Figure 3C:
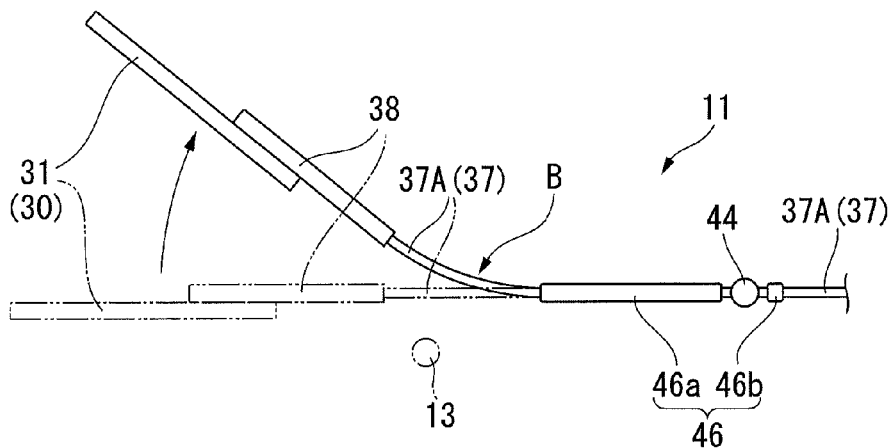
FIG. 3C is an explanatory view for describing the operation of the treatment portion.
Figure 4A:
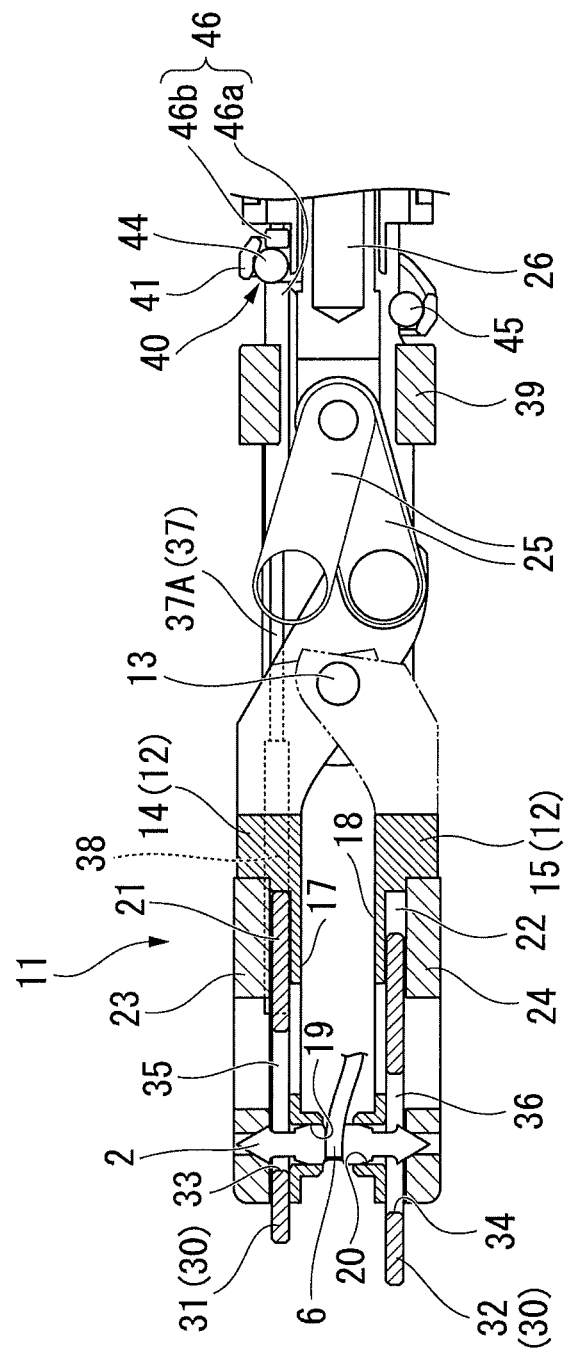
FIG. 4A is a cross-section view taken along line A-A of FIG. 3A.
Figure 4B:
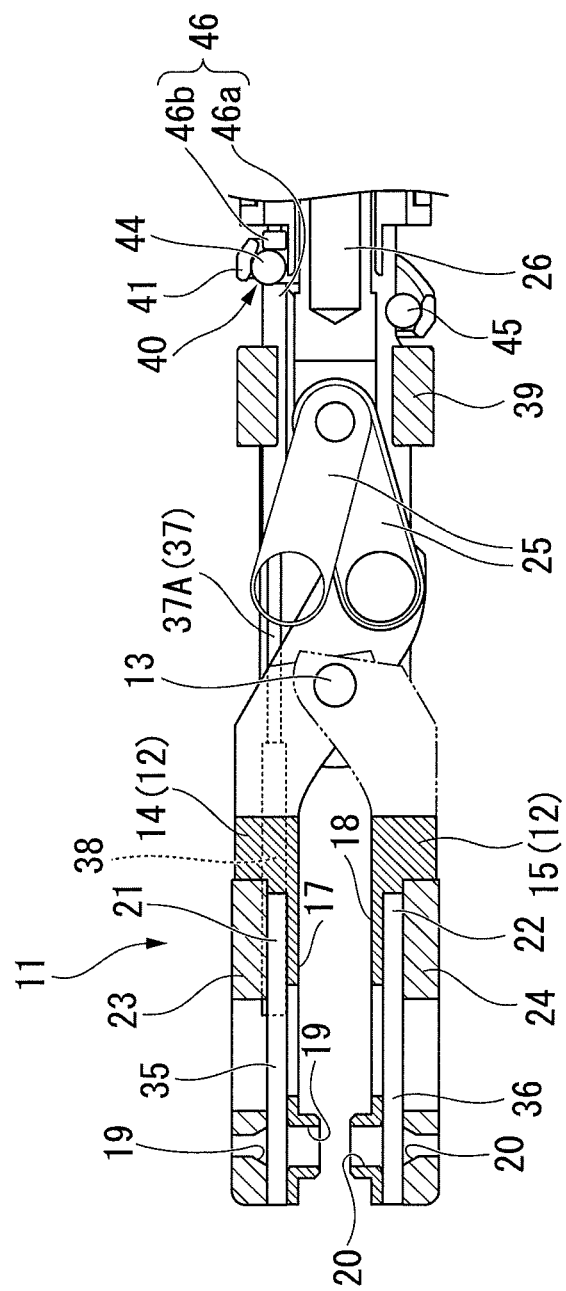
FIG. 4B is a cross-section view showing a state where the suture needle and a needle locking portion are not attached in FIG. 4A.

FIG. 3A is a plan view showing the treatment portion 11 in the suture device 1. FIG. 3B is a plan view showing a partial configuration in the treatment portion 11. FIG. 3C is a view showing the operation of the treatment portion 11 in the suture device 1. FIG. 4A is a cross-section view taken along line A-A of FIG. 3A. FIG. 4B is a cross-section view showing a state where the suture needle 2 and the needle locking portions 30 are detached in FIG. 4A.

As illustrated in FIGS. 3A, 4A, and 4B, the treatment portion 11 has a pair of r members 12, the pair of needle locking portions 30 that are provided at the pair of grasping members 12, a cover member 39 that connects the pair of grasping members 12 to a longitudinal member 50, and a link member 40 that is connected to the longitudinal member 50.

The pair of grasping members 12 includes a first grasping member 14 and a second grasping member 15 that are relatively rotatably connected together by a pin 13 at a proximal end. The first grasping member 14 and the second grasping member 15 rotate relative to each other with a central axis of the pin 13 as a rotation center. This allows the pair of grasping members 12 to perform an opening and closing operation.

The first grasping member 14 is formed with a first grasping surface 17 for grasping living body tissue, and the second grasping member 15 is formed with a second grasping surface 18 for grasping the living body tissue. A depression 19 formed so as to be depressed in a direction orthogonal to the first grasping surface 17 is formed in the first grasping surface 17 in order to support the suture needle 2. A depression 20 formed so as to be depressed in a direction orthogonal to the second grasping surface 18 is formed in the second grasping surface 18 in order to support the suture needle 2.

The depressions 19 and 20 formed in the first grasping surface 17 and the second grasping surface 18 have a shape that resembles the shape of the ends 3 and 4 of the suture needle 2. The ends 3 and 4 of the suture needle 2 fit into the depressions 19 and 20.

Links 25 are respectively connected to proximal ends of the pair of grasping members 12. Moreover, an opening-closing wire 26 (power transmitting member) is fixed to the links 25. The links 25 are provided in order to convert advance/retraction operation of the opening-closing wire 26 into the opening and closing operation of the pair of grasping members 12. The opening-closing wire 26 has a distal end connected to the pair of grasping members 12 via the links 25, and has a proximal end connected to the operating portion 60 (refer to FIG. 1). The opening-closing wire 26 is a wire rod (for example, a stranded wire) fixed to a proximal end of the link 25, and is inserted into a coiled sheath 52 (refer to FIG. 7) inside the longitudinal member 50.

As illustrated in FIGS. 4A and 4B, the pair of needle locking portions 30 are respectively disposed inside the pair of grasping members 12. Specifically, the pair of grasping members 12 are provided with grooves 21 and 22 into which the needle locking portions 30 are inserted, and lids 23 and 24 that close the grooves 21 and 22, respectively.

The grooves 21 and 22 are formed so as to extend from distal ends of the pair of grasping members 12 toward the proximal ends thereof, and distal ends of grooves 21 and 22 are open.

As illustrated in FIGS. 4A and 4B, a first needle locking member 31 that is a plate-like member that constitutes the pair of needle locking portions 30 is inserted into the groove 21.

As illustrated in FIG. 3B, the first needle locking member 31 is formed with a through-hole 33 passed therethrough in a thickness direction and a locking hole portion 35 formed to be connected to the through-hole 33. The through-hole 33 has an internal diameter having almost the same size as the internal diameter of the depression 19 (refer to FIGS. 4A and 4B) formed in the pair of grasping members 12. One of the ends 3 and 4 of the suture needle 2 is insertable into the through-hole 33.

The width of the locking hole portion 35 is smaller than the internal diameter of the through-hole 33 and is greater than the external diameter of the groove portion 5 formed in the suture needle 2. Additionally, the locking hole portion 35 is arranged on the proximal end side of the through-hole 33. Accordingly, if the locking hole portion 35 enters the groove portion 5 of the suture needle 2, one of the ends 3 and 4 of the suture needle 2 is locked to the first needle locking member 31.

As illustrated in FIGS. 4A and 4B, the second needle locking member 32 that is a plate-like member that constitutes the pair of needle locking portions 30 is inserted into the groove 22. The second needle locking member 32 is formed with a through-hole 34 that is the same as the above-described through-hole 33, and a locking hole portion 36 that is the same as the above-described locking hole portion 35. In the present embodiment, the second needle locking member 32 is formed with the same shape and size as the first needle locking member 31. The shapes of the second needle locking member 32 and the first needle locking member 31 may be different from each other.

Additionally, as illustrated in FIG. 3B, distal ends of passing wires 37 (wire members) are fixed to the proximal ends of the pair of needle locking portions 30. That is, a distal end of a first passing wire 37A (first wire member,) is fixed to a proximal end of the first needle locking member 31, and a distal end of a second passing wire 37B (second wire member) is fixed to a proximal end of the second needle locking member 32. The passing wire 37 is arranged at a position apart from the link 25 so as to avoid the link 25.

In the passing wire 37, a range from the pin 13, which connects the pair of grasping members 12 together and is an opening-closing shaft in the pair of grasping members 12, to the distal end of the passing wire 37 is covered with a hard pipe 38. Accordingly, the passing wire 37 has flexibility in a portion B (refer to FIGS. 3A, 3B, and 3C) that is bent by the opening and closing operation of the pair of grasping members 12 (refer to FIG. 3A), and has high rigidity such that the passing wire does not easily buckle closer to the distal end side than the portion B. The pipe 38 that covers the passing wire 37 may be a material that is harder than the passing wire 37, or may be a pipe that has the same hardness as the passing wire 37. That is, the pipe 38 that covers the passing wire 37 just has to be capable of reinforcing the passing wire 37.

The cover member 39 is a tubular member that is fixed to a distal end of the longitudinal member 50. The cover member 39 holds both ends of the pin 13. The links 25 and the opening-closing wire 26 that open and close the pair of grasping members 12 are inserted into the cover member 39.

An outer peripheral surface of the cover member 39 is formed with a slit 39a for keeping the pair of grasping members 12 and the links 25 from interfering with the cover member 39 during the opening and closing operation of the pair of grasping members 12.

Figure 5:
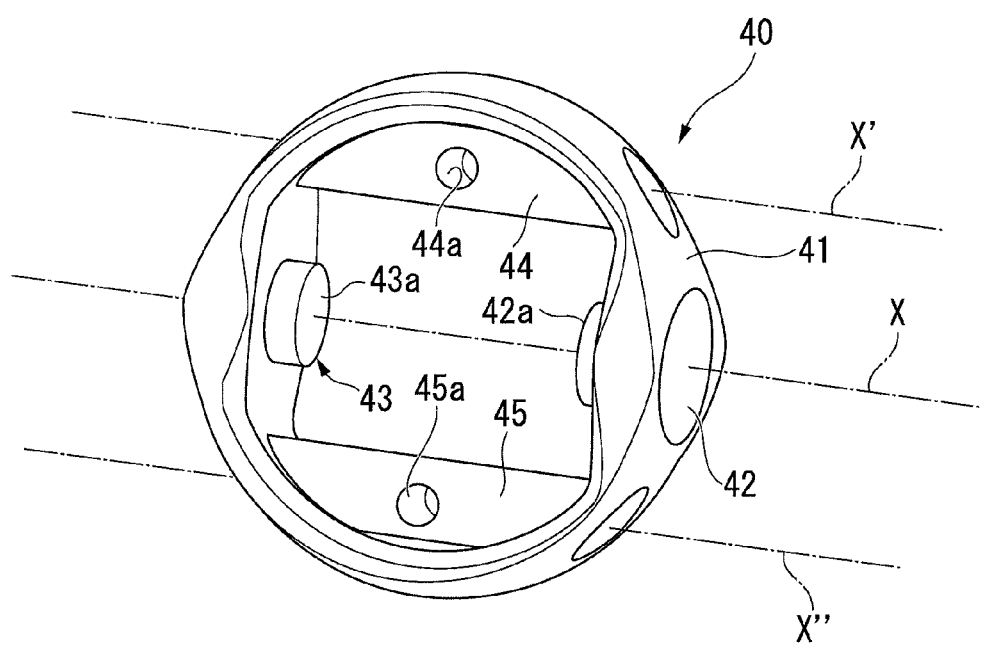
FIG. 5 is a perspective view showing a link member.

FIG. 5 is a perspective view showing the link member 40. As illustrated in FIG. 5, the link member 40 has an annular body 41, rotatable supporting portions 42 and 43, and a pair of connecting portions 44 and 45.

As illustrated in FIGS. 3A, 4A, and 4B, the body 41 is rotated with respect to the cover member 39 with a central axis of the rotatable supporting portions 42 and 43 as a rotation center. The opening-closing wire 26 and the passing wires 37 are inserted inside the body 41 that is annularly formed.

As illustrated in FIG. 5, the rotatable supporting portions 42 and 43 are formed in a columnar shape of which a central axis extends in a direction intersecting the longitudinal axis of the longitudinal member 50. In addition, the shape of the rotatable supporting portions 42 and 43 may be shapes other than the columnar shape without being limited to the columnar shape. The rotatable supporting portions 42 and 43 are provided for the purpose of connecting the body 41 to the cover member 39. In the present embodiment, the central axis X of the rotatable supporting portions 42 and 43 is directed to the direction orthogonal to the longitudinal axis of the longitudinal member 50. Additionally, the rotatable supporting portions 42 and 43 are arranged in two places that face each other with the center of the annular body 41 therebetween.

The rotatable supporting portions 42 and 43 are fixed to the body 41. Moreover, ends 42a and 43a directed to the inside of the body 41 in the rotatable supporting portions 42 and 43 are inserted into the cover member 39 (refer to FIG. 3A). Accordingly, as illustrated in FIG. 3A, the body 41 is connected to the cover member 39 by the rotatable supporting portions 42 and 43. That is, in the present embodiment, the rotatable supporting portions 42 and 43 connect the link member 40 and the longitudinal member 50 via the cover member 39.

As illustrated in FIG. 5, the connecting portions 44 and 45 are two rod-shaped members that extend parallel to each other, and the passing wires 37 are inserted into the body 41. Respective rod-shaped members that constitute the connecting portions 44 and 45 are relatively rotatable with respect to the body 41 with respective central axes X' and X" as rotation centers.

The center of each rod-shaped member in a central axis direction is formed with a hole 44a or 45a of which a centerline extends in a direction orthogonal to the central axis. The two passing wires 37 (the first passing wire 37A and the second passing wire 37B) are respectively inserted into the holes 44a and 45a formed in the respective rod-shaped members that constitute the connecting portions 44 and 45.

Since the body 41 and the connecting portions 44 and 45 can be relatively moved, the connecting portions 44 and 45 maintain the passing wires 37 substantially parallel to the longitudinal axis of the longitudinal member 50 regardless of the rotational angle of the body 41 itself.

The connecting portions 44 and 45 may not be the rod-shaped members, and the same effects are obtained as long as the connecting portions are relatively rotatable with respect to the body 41.

As illustrated in FIGS. 4A and 4B, a tubular member 46 is fixed to the passing wire 37A inserted into the holes 44a of the connecting portions 44. In addition, although not illustrated, the second passing wire 37B is also provided with the same configuration as the tubular member 46.

The passing wire 37 is inserted into the tubular member 46. Moreover, the tubular member 46 abuts against an opening end of the hole 44a at that is formed in the connecting portion 44. As the tubular member 46 abuts against the opening end of the connecting portion 44, the passing wire 37 is positioned with respect to the connecting portion 44. A tubular member 46a of the tubular member 46 disposed on the distal end side of the connecting portion 44 is fixed to the passing wire 37 by a fixing method having strength such that the passing wire 37 can withstand a pulling force when being towed to the proximal end side. Additionally, a tubular member 46b of the tubular member 46 disposed on the proximal end side of the connecting portion 44 is fixed to the passing wire 37 by a fixing method having strength such that the passing wire 37 can withstand a pressing force when being pressed to the distal end side by the connecting portion 44.

A frictional resistance caused on the passing wire 37 closer to the proximal end side than the link member 40 is greater than a frictional resistance caused on the passing wire 37 closer to the distal end side than the link member 40. Particularly, if the length of the longitudinal member 50 increases, a frictional resistance to the passing wire 37 within the longitudinal member 50 increases. Thus, a difference in magnitude between the frictional resistances becomes remarkable. For this reason, in the present embodiment, a fixing method in which the tubular member 46a disposed on the distal end side of the connecting portion 44 or 45 has a higher strength than the tubular member 46b disposed on the proximal end side of the connecting portion 44 or 45 is adopted. Specifically, in the present embodiment, the tubular member 46a disposed on the distal end side of the connecting portion 44 or 45 is fixed to the passing wire 37 by laser welding. Additionally, in the present embodiment, the tubular member 46b disposed on the proximal end side of the connecting portion 44 or 45 is fixed to the passing wire 37 by brazing or the like. In addition, the fixing methods of the respective tubular members 46 to the passing wires 37 may be different from the fixing methods in consideration of workability.

Figure 6:
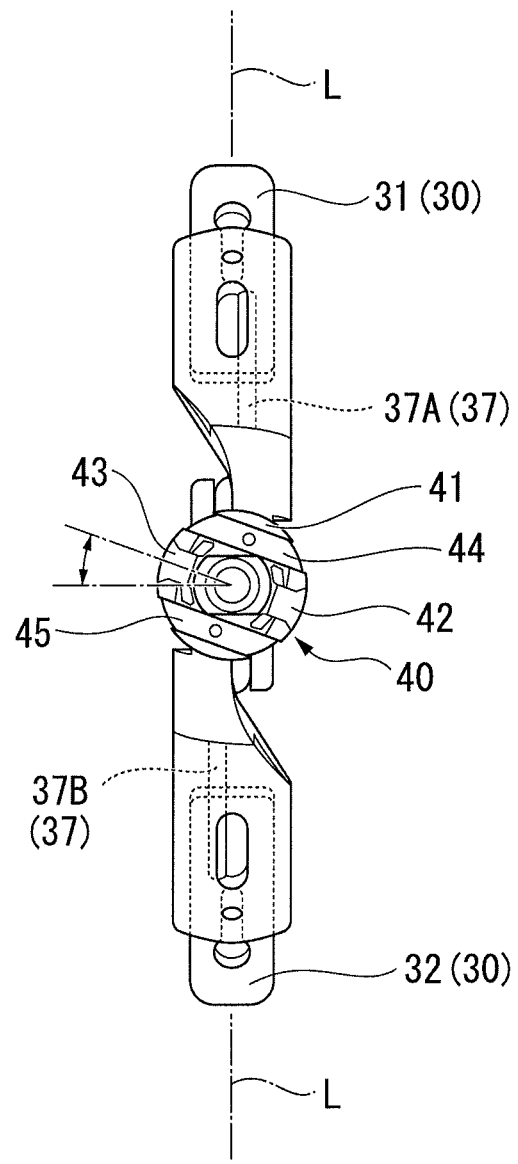
FIG. 6 is a front view of the treatment portion.

FIG. 6 is a front view of the treatment portion. In addition, in FIG. 6, in order to emphasize the positional relationship of the link member 40, the link member 40 that is hidden by the pair of grasping members 12, the cover member 39, or the like and is originally invisible is deliberately illustrated. As illustrated in FIG. 6, in the present embodiment, the link member 40 has a positional relationship in which the whole link member 40 is shifted in a circumferential direction with respect to a median line L of the pair of grasping members 12. When the pair of grasping members 12 are in a fully closed state, the passing wires 37 are brought into a linear state of being parallel to the longitudinal axis of the longitudinal member 50, in the regions from the pair of grasping members 12 to the holes 44a and 45a of the connecting portions 44 and 45.

Figure 7:
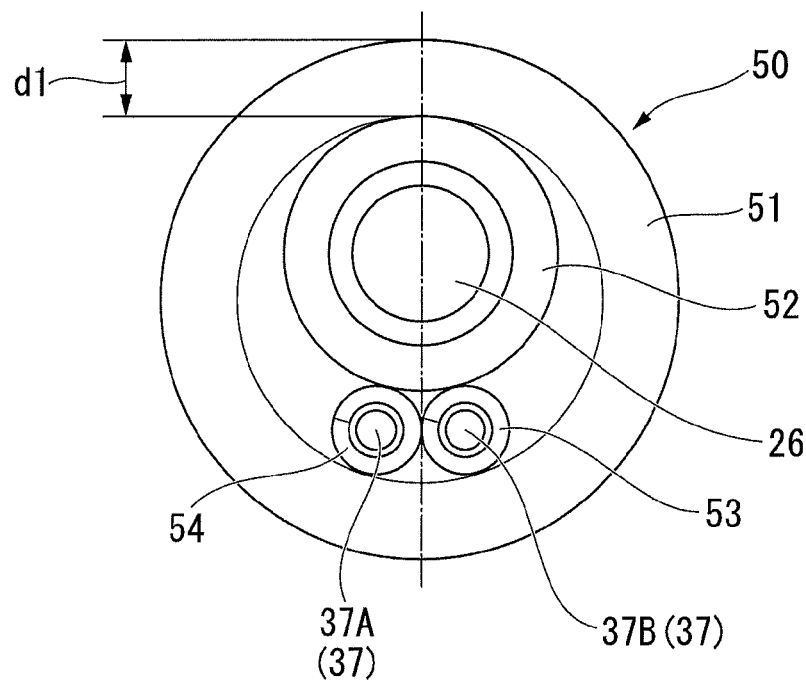
FIG. 7 is a cross-section view showing a cross-portion orthogonal to a longitudinal axis of a longitudinal member.

FIG. 7 is a cross-section view showing a cross-portion orthogonal to the longitudinal axis of the longitudinal member. As illustrated in FIG. 7, the longitudinal member 50 has an outer sheath 51 made of resin, and the coiled sheath 52 inserted into the outer sheath 51. The outer sheath 51 and the coiled sheath 52 that constitute the longitudinal member 50 are flexible members having the longitudinal axis.

The outer sheath 51 is a tubular member that has an external diameter such that the outer sheath is insertable through a treatment tool channel (designated by reference numeral 101 in FIG. 1) of the endoscope. An outer surface of the outer sheath 51 is in a surface state where a frictional resistance to the inner surface of the treatment tool channel 101 is low.

The coiled sheath 52 is a sheath in which a wire rod is wound in a coil form with the longitudinal axis of the longitudinal member 50 as a center, and is a sheath in which flexibility, and resistance against compression in the direction of the longitudinal axis are balanced. The opening-closing wire 26 is inserted into the coiled sheath 52.

A centerline of the outer sheath 51 is shifted in parallel from a centerline of the coiled sheath 52. Moreover, in the present embodiment, second coiled sheaths 53 and 54 are arranged between the outer sheath 51 and the coiled sheath 52.

Figure 8:
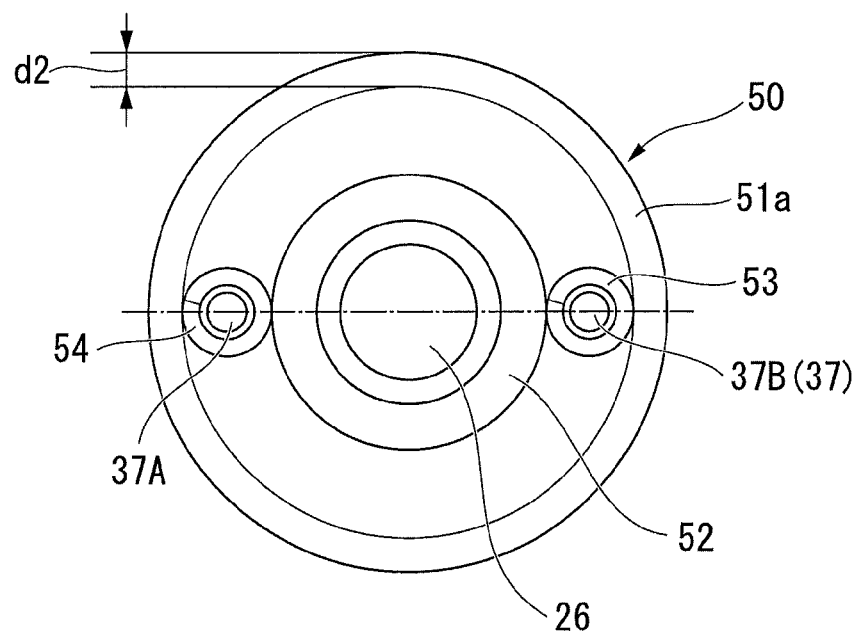
FIG. 8 is a reference view for comparison with the configuration illustrated in FIG. 7.

The second coiled sheaths 53 and 54 are tubular members through which the passing wires 37 are inserted. The second coiled sheaths 53 and 54 are arranged adjacent to each other inside the longitudinal member 50. Accordingly, as compared to a case where the second coiled sheaths 53 and 54 are disposed at positions that face each other in a radial direction of the coiled sheath 52, the maximum external diameter of a bundle of the coiled sheath 52 and the second coiled sheaths 53 and 54 can be made smaller. Accordingly, for example, as illustrated in FIG. 8, as compared to the wall thickness d2 of an outer sheath 51a when the second coiled sheaths 53 and 54 are disposed at positions that face each other with the coiled sheath 52 therebetween, the wall thickness d1 of the outer sheath 51 can be increased without enlarging the external diameter of the outer sheath 51, as illustrated in FIG. 7. For this reason, reduction in the diameter of the longitudinal member 50, and buckling prevention of the longitudinal member 50 can be made compatible.

Additionally, opening ends of the second coiled sheaths 53 and 54 on the distal end side are disposed at positions apart further toward the proximal end side than the link member 40. The passing wires 37 extending from the opening ends of the second coiled sheaths 53 and 54 on the distal end side respectively extend toward the holes 44a and 45a formed in the respective connecting portions 44 and 45 provided in the link member 40 (refer to FIGS. 4A and 4B).

As illustrated in FIG. 1, the operating portion 60 includes a first slider 61 for pushing and pulling the opening-closing wire 26, and second sliders 62 and 63 for pulling the passing wires 37, respectively. The proximal end of the opening-closing wire 26 is fixed to the first slider 61. The second slider 62 is a slider for pulling the first passing wire 37A. The second slider 63 is a slider for pulling the second passing wire 37B. Proximal ends of the passing wires 37 are fixed to the second sliders 62 and 63, respectively.

In the present embodiment, the operating portion 60 is an opening-closing operating portion that performs the operation of transmitting power to the opening-closing wire 26 in order to perform the opening and closing operation of the pair of grasping members 12, and is a needle locking and operating portion that performs the operation of moving the passing wires 37 along the longitudinal axis of the longitudinal member 50, to lock or release the suture needle 2 to or from the needle locking portions 30.

The configuration of the operating portion 60 is not limited to the configuration that has the first slider 61 and the second sliders 62 and 63. For example, a configuration in which the opening-closing wire 26 or the passing wires 37 are moved using a lever, a configuration in which the opening-closing wire 26 or the passing wires 37 are wound around a rotating shaft and moved, or the like may be adopted as the operating portion 60.

Figure 9:
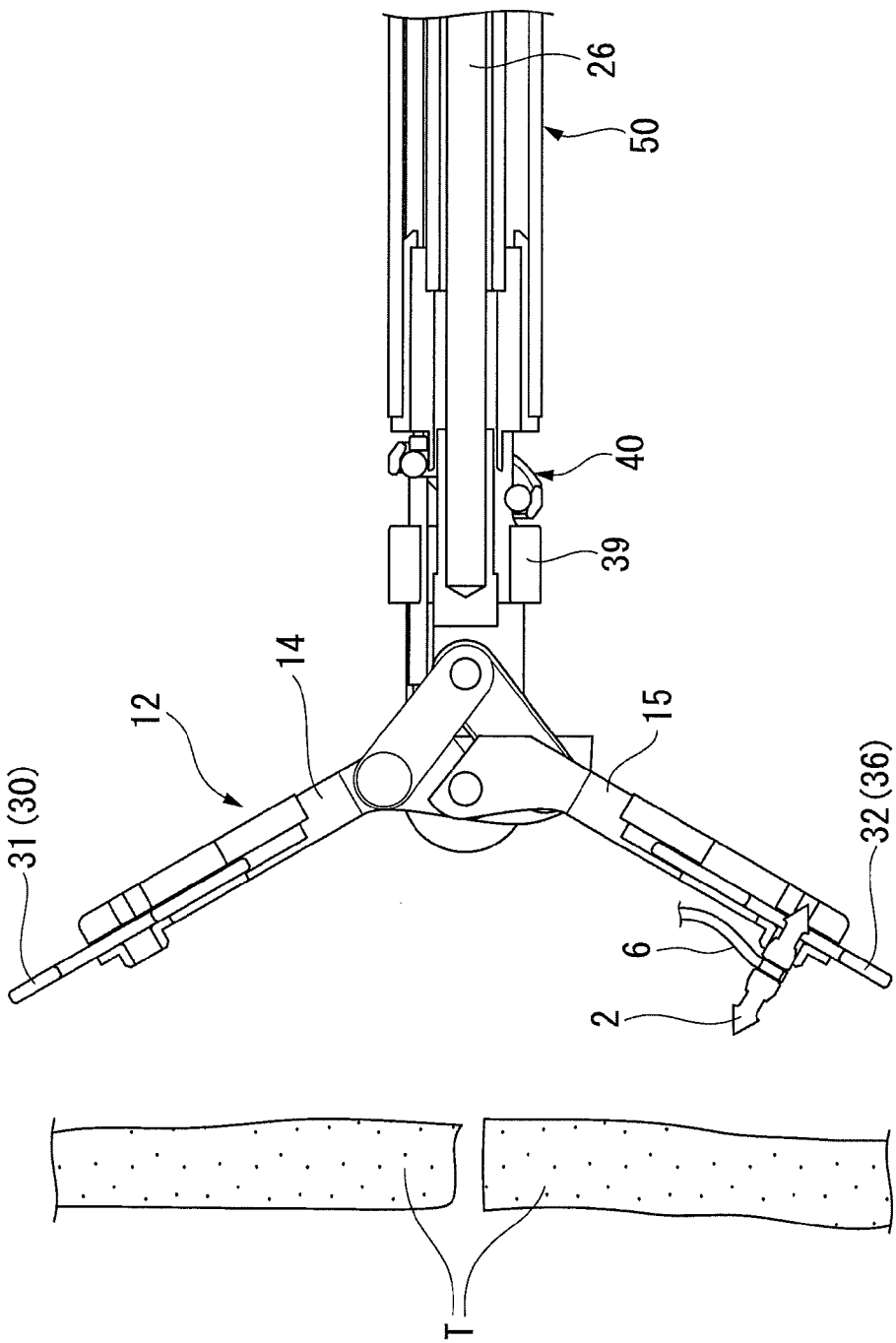
FIG. 9 is an explanatory view showing a process when the suture device is used.
Figure 10:
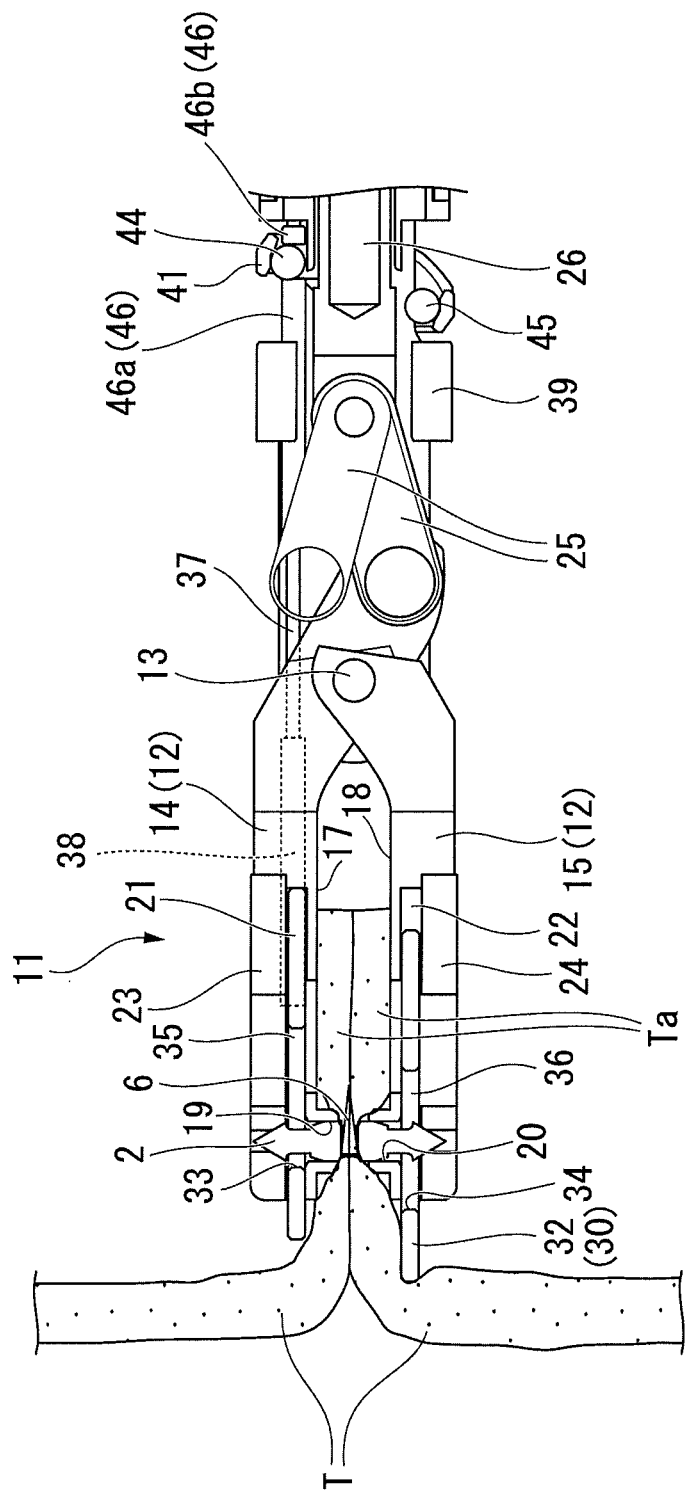
FIG. 10 is an explanatory view showing the process when the suture device is used.
Figure 11:
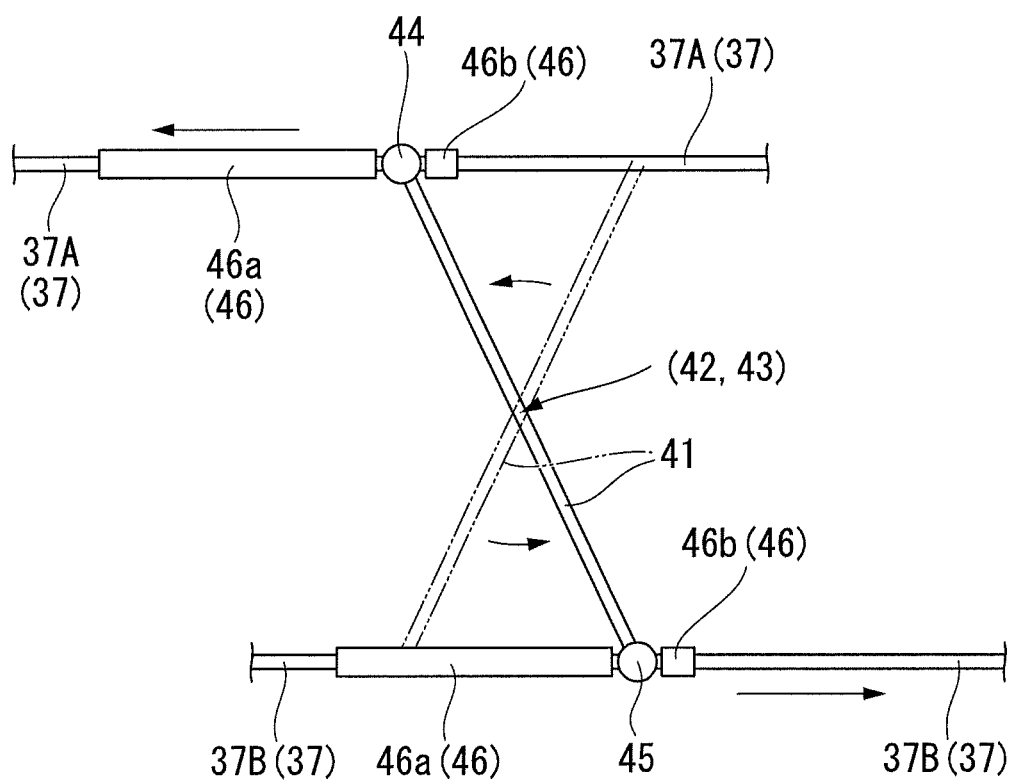
FIG. 11 is a schematic view for describing the actions of the suture device.

Next, the operation and actions when the suture device 1 of the present embodiment is used will be described. FIGS. 9 and 10 are explanatory views showing a process when the suture device 1 is used. FIG. 11 is a schematic view for describing the actions of the suture device 1.

The suture device 1 is prepared in a state where the suture needle 2 is attached to one of a pair of grasping members 12 (the second grasping member 15 in FIG. 9) provided in the suture device 1. The suture device 1, as illustrated in FIG. 1, is inserted into the treatment tool channel 101 of the endoscope 100 from the treatment portion 11 side, and is guided to a target region that is a target where living body tissue is to be sutured.

If the treatment portion 11 is guided to a part T that is a suturing target, living body tissue located at the part T that is the suturing target is gripped by pulling the first slider 61 illustrated in FIG. 1 to close the pair of grasping members 12 as illustrated in FIG. 10. If the pair of grasping members 12 are closed, the suture needle 2 attached to one (second grasping member 15) of the pair of grasping members 12 enter the depression (depression 19) formed in the grasping surface (first grasping surface 17) of the other (first grasping member 14) of the pair of grasping members 12. Accordingly, the living body tissue Ta that is present between the grasping surfaces 17 and 18 arranged to face each other in the pair of grasping members 12 is punctured by the suture needle 2.

Additionally, in the suture device 1 of the present embodiment, if the pulling force of the first slider 61 illustrated in FIG. 1 is lessened, the grasping of the living body tissue between the first grasping surface 17 and the second grasping surface 18 is released. Additionally, if the first slider 61 is moved to the distal end side, the pair of grasping members 12 are opened. In this case, the suture needle 2 is still in a state where the suture needle is attached to the second grasping member 15. Accordingly, the living body tissue can be punctured again by the suture needle 2. In addition, the living body tissue can be moved or the orientation of the living body tissue can also be changed similar to grasping forceps that only grips the living body tissue, by grasping the living body tissue with a force of such a degree that the suture needle 2 does not penetrate the living body tissue while pulling the first slider 61.

In order to suture the living body tissue using the suture needle 2 to which the suture 6 is attached, the suture needle 2 is pulled out from a side where puncturing is made by the suture needle 2 to a side opposite to the puncturing side, in a state where the living body tissue is punctured by the suture needle 2. In this case, a slider, which is located closer to the distal end side out of the two sliders provided as the second sliders 62 and 63 in the operating portion 60 illustrated in FIG. 1, is pulled by manual work or the like. In the present embodiment, the second slider 63 to which the second passing wire 37B is fixed is pulled.

Accordingly, on the distal end side of the longitudinal member 50, as illustrated in FIG. 11, the connecting portion 45 of the link member 40 is moved to the proximal end side. Since the link member 40 is rotatable with respect to the cover member 39 by the rotatable supporting portions 42 and 43, if the connecting portion 45 is moved to the proximal end side, the connecting portion 44 is reversely moved to the distal end side. That is, the portion of the first passing wire 37A closer to the distal end side than the link member 40 is pressed to the distal end side, and the portion of the first passing wire 37A closer to the proximal end side than the link member 40 is pulled to the distal end side. That is, the first passing wire 37A is moved to the distal end side as a whole by the action of the link member 40.

Inside the pair of grasping members 12, the first needle locking member 31 to which the distal end of the first passing wire 37A is fixed is pressed by the first passing wire 37A and is moved to the distal end side. Then, the first needle locking member 31 moves so that the locking hole portion 35 enters the groove portion 5. Accordingly, the suture needle 2 is locked to the first needle locking member 31.

Additionally, the second needle locking member 32 to which the distal end of the second passing wire 37B is fixed is moved to the proximal end side by pulling the second passing wire 37B. Then, the second needle locking member 32 moves so that the locking hole portion 36 separates from the groove portion 5. Accordingly, the suture needle 2 can be removed from the second needle locking member 32.

If the pair of grasping members 12 are opened by moving the first slider 61 to the distal end side in this state, the suture needle 2 moves in a state where the suture needle is locked to the first grasping member 14, penetrates the living body tissue, and is pulled out. As a result, the suture 6 fixed to the suture needle 2 is inserted into the living body tissue.

Additionally, in the present embodiment, when the treatment portion 11 is seen in a plan view, the first passing wire 37A is located closer to the first grasping member 14 side than the pin 13, and the second passing wire 37B is located closer to the second grasping member 15 side than the pin 13. Accordingly, when the pair of grasping members 12 are opened, the pair of needle locking portions 30 are pressed so that the pair of needle locking portions 30 relatively advance with respect to the pair of grasping members 12. As a result, the locking hole portion of the first needle locking member 31 or the second needle locking member 32 enters the groove portion 5 formed in the suture needle 2, and the suture needle 2 does not come off in slight advance/retraction movement of the second sliders 62 and 63.

Then, the suture 6 is tied if necessary and a series of treatment is ended. In addition, the suture 6 may be inserted again into the living body tissue if necessary after the suture needle 2 is passed from the second grasping member 15 to the first grasping member 14.

In summary, when the suture needle is passed from the second grasping member 15 to the first grasping member 14, the pair of grasping members 12 are closed, and the second passing wire 37B is moved to the proximal end side in the operating portion 60. Accordingly, the suture needle 2 can be removed from the second needle locking member 32 provided at the second grasping member 15, and simultaneously, the suture needle 2 is locked to the first grasping member 14 by the first needle locking member 31 provided at the first grasping member 14.

The suture device 1 of the present embodiment can grip living body tissue in order to suture the living body tissue and pass the suture needle 2 between the pair of grasping members 12, and can also open the grasping members 12 again without passing the suture needle 2 once the living body tissue is gripped. Accordingly, a function as forceps that grips living body tissue, and a function as a device that sutures the living body tissue can be made compatible.

Additionally, since the suture device 1 can be inserted into a treatment tool channel of a flexible endoscope and the suture device 1 can be used, a treatment tool of the suture device 1 can be easily guided to a part to be sutured in a case where a part that requires suturing of living body tissue is discovered when examination is performed using the flexible endoscope.

Particularly, in endoscopes in which only one treatment tool channel is provided, living body tissue in the vicinity of a part to be sutured can be moved or the part to be sutured can be sutured without separately preparing grasping forceps. Thus, working efficiency is excellent. Additionally, once living body tissue is gripped, a suturing position can be easily changed.

While an example of the preferred embodiment of the present invention has been described above, the present invention is not limited to the above embodiment. Additions, omissions, substitutions, and other modifications of components can be made without departing from the concept of the present invention.

The invention claimed is:

1. A suture device comprising:
 a longitudinal member extending along a longitudinal axis;
 a pair of grasping members capable of opening and closing, and being provided at a distal end of the longitudinal member;
 a pair of needle locking portions capable of locking a suture needle to the pair of grasping members;
 a first wire member configured to move along the longitudinal member and having flexibility, the first wire member including:
  a distal end connected to one of the pair of needle locking portions, and
  a proximal end extending to a proximal end of the longitudinal member and that is continuously provided in the distal end;
 a second wire member configured to move along the longitudinal member and having flexibility, the first wire member including:
  a distal end that is connected to the other of the pair of needle locking portions, and
  a proximal end that extends to a proximal end of the longitudinal member and that is continuously provided in the distal end;
 an operating portion provided in the proximal end of the first wire member and the second wire member, and being capable of operating to pull the first wire member and the second wire member;
 an annular link member having a body and being configured to rotate with respect to the longitudinal member about a central axis orthogonal to the longitudinal axis, the annular link member including: (i) a first connecting portion connected between the distal end of the first wire member and the operating portion, and (ii) a second connecting portion connected between the distal end of the second wire member and the operating portion, the first connecting portion and the second connecting portion being located at a position which departs from a median line of the pair of grasping members along a circumferential direction, wherein:
 in response to the second wire member being pulled toward the operating portion: (1) a portion of the second wire member that is closer to the distal end than the second connecting portion of the link member pulls the other of the pair of needle locking portions toward the operating portion, (2) the link member rotates about the central axis, and (3) a portion of the first wire member closer to the proximal end than the first connecting portion of the link member is pulled toward the link member.

2. The suture device according to claim 1, wherein:
 the longitudinal member is flexible, and
 the suture device includes an opening-closing shaft configured to open and close the pair of grasping members, and
 a range from a distal end of the first wire member to the opening-closing shaft and a range from a distal end of the second wire member to the opening-closing shaft are respectively inserted through pipes that are harder than the first wire member and the second wire member.

3. The suture device according to claim 1, wherein:
 the pair of grasping members have a conical depression for supporting the suture needle, and
 the suture needle has a conical end that fits into the depression, and a groove portion that is adjacent to the end and has a diameter smaller than the end, and
 the pair of needle locking portions have a through-hole through which the end is capable of being inserted, and a locking hole portion that is formed so as to be connected to the through-hole, and has a width that is smaller than the internal diameter of the through-hole and greater than the external diameter of the groove portion.

4. The suture device according to claim 1, further comprising:
 a cover member which is provided in a distal end of the longitudinal member and includes an inner space, wherein:
 the pair of grasping members are held to be capable of opening and closing at a distal side of the inner space, and
 the link member is held by an outer periphery of the proximal end of the cover member to be capable of rotating at a proximal end of the cover member.

5. The suture device according to claim 4, further comprising:
 a power transmitting member which is provided to be capable of moving at the inner space of the cover member along the longitudinal member with respect to both of the first wire member and the second wire member and performs the opening and closing operation of the pair of grasping members.

6. The suture device according to claim 5, wherein:
 the power transmitting member is provided to be capable of moving inside the link member, and
 the suture device includes:
  a grasping opening-closing link that is connected to a distal end portion of the power transmitting member, and
  an opening-closing shaft that allows a proximal end of the pair of grasping members to be connected to the grasping opening-closing link and the cover member, the opening-closing shaft being capable of opening and closing the pair of grasping members.

7. The suture device according to claim 4, wherein:
 the link member has a rotatable supporting portion that extends toward the cover member, and
 a central axis of the rotatable supporting portion extends in a direction intersecting the longitudinal axis.

8. The suture device according to claim 7, wherein:
 the first connecting portion and the second connecting portion are fixed to the body, so as to be rotatable with respect to the body, with an axis parallel to the central axis of the rotatable supporting portion as a center of rotation, a first hole, through which the first wire member is capable of being inserted, is formed in the first connecting portion, and
a second hole, through which the second wire member is capable of being inserted, is formed in the second connecting portion.

9. The suture device according to claim 8, wherein:
tubular members, which abut against opening ends of the holes and position the first wire member and the second wire member with respect to the first connecting portion and the second connecting portion, are attached to the first wire member and the second wire member.

10. The suture device according to claim 4, wherein:
the longitudinal member is flexible, and
the body has an annular shape that has a space into which the cover member is insertable.

11. The suture device according to claim 1, further comprising:
a first tubular member which fixes the first connecting portion and the first wire member at a position between the distal end of the first wire member and the operating portion, and
a second tubular member which fixes the second connecting portion and the second wire member at a position between the distal end of the second wire member and the operating portion.

12. A suture device comprising:
a longitudinal member that is provided to extend along a longitudinal axis;
a cover member that is provided at a distal end of the longitudinal member and includes an inner space;
a pair of grasping members that are capable of opening and closing at a distal side of the inner space;
a pair of needle locking portions that are capable of locking a suture needle to the pair of grasping members;
a first wire member that is flexible and being arranged so as to be capable of moving along the longitudinal member, the first wire including:
a distal end connected to one of the pair of needle locking portions, and
a proximal end that extends to a proximal end of the longitudinal member and that is continuously provided in the distal end of the first wire;
a second wire member that is flexible and being arranged so as to be capable of moving along the longitudinal member, the second wire including:
a distal end that is connected to the other of the pair of needle locking portions, and
a proximal end that extends to a proximal end of the longitudinal member and that is continuously provided in the distal end of the second wire;
an operating portion provided in the proximal end of the first wire member and the second wire member, and the operating portion being capable of pulling the first wire member and the second wire member;
an annular link member having a body and being configured to rotate with respect to the longitudinal member about a central axis orthogonal to the longitudinal axis, the annular link member including: (i) a first connecting portion fixed between the distal end of the first wire member and the operating portion, the first connecting portion having a first through-hole through which the first wire member is insertable, and (ii) a second connecting portion fixed between the distal end of the second wire member and the operating portion, the second connecting portion having a second through-hole through which the second wire member is insertable, the first through-hole and the second through-hole being located at a position that departs from a median line of the pair of grasping members along a circumferential direction, wherein:
in response to the second wire member being pulled toward the operating portion: (1) a portion of the second wire member closer to the distal end than the second connecting portion of the link member pulls the other of the pair of needle locking portions toward the operating portion, (2) the link member rotates about the central axis, and (3) a portion of the first wire member closer to the proximal end than the first connecting portion of the link member is pulled toward the link member.

13. The suture device according to claim 12, further comprising:
a power transmitting member which is provided to be capable of moving at the inner space of the cover member along the longitudinal member with respect to both of the first wire member and the second wire member and performs the opening and closing operation of the pair of grasping members.

14. The suture device according to claim 13, wherein:
the power transmitting member is capable of moving inside the link member, and
the suture device includes a grasping opening-closing link that is connected to a distal end portion of the power transmitting member and an opening-closing shaft that allows a proximal end of the pair of grasping members to be connected to the grasping opening-closing link and the cover member and that is configured to open and close the pair of grasping members.

15. The suture device according to claim 12, wherein:
the link member has a rotatable supporting portion that extends toward the cover member, and
a central axis of the rotatable supporting portion extends in a direction intersecting the longitudinal axis.

16. The suture device according to claim 15, wherein:
the first connecting portion and the second connecting portion are connected to the body, so as to be rotatable with respect to the body, with an axis parallel to the central axis of the rotatable supporting portion as a center of rotation,
a first hole, through which the first wire member is capable of being inserted, is formed in the first connecting portion, and
a second hole, through which the second wire member is capable of being inserted, is formed in the second connecting portion.

17. The suture device according to claim 16, wherein:
tubular members, which abut against opening ends of the holes and position the first wire member and the second wire member with respect to the first connecting portion and the second connecting portion, are attached to the first wire member and the second wire member.

18. The suture device according to claim 15, wherein:
the rotatable supporting portion connects the link member and the longitudinal member via the cover member, and
the central axis of the rotatable supporting portion is located between the first connecting portion and the second connecting portion orthogonal to the longitudinal axis of the longitudinal member.

19. The suture device according to claim 15, wherein:
the first connecting portion and the second connecting portion are fixed to the body so as to be rotatable with respect to the body, with an axis parallel to the central axis of the rotatable supporting portion.

20. The suture device according to claim 12, wherein:
the longitudinal member has flexibility, and
the body has an annular shape that has a space into which the cover member is insertable.

* * * * *